United States Patent
Shiodera (10) Patent No.: US 10,698,060 B2
(45) Date of Patent: Jun. 30, 2020

(54) MAGNETIC RESONANCE IMAGING APPARATUS AND MEDICAL IMAGE PROCESSING APPARATUS

(71) Applicant: Canon Medical Systems Corporation, Otawara-shi (JP)

(72) Inventor: Taichiro Shiodera, Tokyo (JP)

(73) Assignee: Canon Medical Systems Corporation, Otawara-shi (JP)

( * ) Notice: Subject to any disclaimer, the term of this patent is extended or adjusted under 35 U.S.C. 154(b) by 9 days.

(21) Appl. No.: 16/015,324

(22) Filed: Jun. 22, 2018

(65) Prior Publication Data

US 2018/0372827 A1 Dec. 27, 2018

(30) Foreign Application Priority Data

Jun. 26, 2017 (JP) ................. 2017-124480

(51) Int. Cl.
| | |
|---|---|
| G01R 33/561 | (2006.01) |
| A61B 5/053 | (2006.01) |
| G01R 33/24 | (2006.01) |
| A61B 5/055 | (2006.01) |
| A61B 5/00 | (2006.01) |
| G01R 33/44 | (2006.01) |
| G01R 33/565 | (2006.01) |
| G01R 33/48 | (2006.01) |

(52) U.S. Cl.
CPC .......... *G01R 33/5615* (2013.01); *A61B 5/055* (2013.01); *A61B 5/0536* (2013.01); *A61B 5/0555* (2013.01); *A61B 5/7257* (2013.01); *G01R 33/243* (2013.01); *G01R 33/443* (2013.01); *A61B 5/0042* (2013.01); *G01R 33/48* (2013.01); *G01R 33/5616* (2013.01); *G01R 33/56536* (2013.01)

(58) Field of Classification Search
CPC ............................ G01R 33/5615; A61B 5/055
USPC ........................................................ 324/309
See application file for complete search history.

(56) References Cited

U.S. PATENT DOCUMENTS

| | | | | |
|---|---|---|---|---|
| 2011/0234222 | A1* | 9/2011 | Frahm ................ | G01R 33/4824 324/309 |
| 2014/0184219 | A1 | 7/2014 | Kim et al. | |
| 2015/0276903 | A1* | 10/2015 | Taniguchi ............ | G01R 33/243 324/318 |
| 2017/0097399 | A1 | 4/2017 | Shiodera et al. | |

FOREIGN PATENT DOCUMENTS

JP          2017-70386          4/2017

OTHER PUBLICATIONS

Extended European Search Report dated Mar. 21, 2019 in European Patent Application No. 18179140.1, 15 pages.

(Continued)

*Primary Examiner* — Reena Aurora
(74) *Attorney, Agent, or Firm* — Oblon, McClelland, Maier & Neustadt, L.L.P.

(57) ABSTRACT

According to one embodiment, the magnetic resonance imaging apparatus has a processing circuitry. The processing circuitry generates a conductivity map quantitatively indicating the conductivity in the subject using a susceptibility map quantitatively indicating the susceptibility in the subject.

11 Claims, 7 Drawing Sheets

(56) References Cited

OTHER PUBLICATIONS

Katscher, U., et al., "Conductivity Determination of Deep Gray Matter Nuclei Utilizing Susceptibility-Based Delineation" International Society for Magnetic Resonance in Medicine, No. 3336, XP040684377, Apr. 22, 2016, 3 pages.

Katscher, U., et al., "Recent Progress and Future Challenges in MR Electric Properties Tomography", Computational and Mathematical Methods in Medicine, vol. 2013, XP055352311, Mar. 7, 2013, pp. 1-11 with cover page.

Kim, D.-H., et al., "Simultaneous Imaging of In Vivo Conductivity and Susceptibility", Magnetic Resonance in Medicine, vol. 71 No. 3, XP055565706, Apr. 19, 2013, pp. 1144-1150.

Gho. S.-M., et al., "Simultaneous Quantitative Mapping of Conductivity and Susceptibility Using a Double-Echo Ultrashort Echo Time Sequence: Example Using a Hematoma Evolution Study", Magnetic Resonance in Medicine, vol. 76 No. 1, XP055565704, Aug. 24, 2015, pp. 214-221.

\* cited by examiner

MAGNETIC RESONANCE IMAGING APPARATUS AND MEDICAL IMAGE PROCESSING APPARATUS

CROSS-REFERENCE TO RELATED APPLICATIONS

This application is based upon and claims the benefit of priority from the prior Japanese Patent Application No. 2017-124480, filed Jun. 26, 2017, the entire contents of which are incorporated herein by reference.

FIELD

Embodiments described herein relate generally to a magnetic resonance imaging apparatus and a medical imaging processing apparatus.

BACKGROUND

In the magnetic resonance imaging apparatus, there is a technique of non-invasive quantification of electromagnetic properties of a tissue based on a phase image. In particular, a Quantitative Conductivity Mapping (QCM), which calculates quantitative conductivity using a phase value where an echo time will be zero, based on linearity of the phase value to the echo time TE from MR (Magnetic Resonance) data of a subject that was imaged by a gradient echo method, is known. By the conductivity map, which maps the conductivity of the tissue, for example, tumor grading becomes possible. Also, the conductivity map is used for calculation of a local SAR (Specific Absorption Rate).

A Quantitative Susceptibility Mapping (QSM), which calculates a quantitative susceptibility using an inclination of a phase value to the echo time based on linearity of phase value to the echo time from MR data, is known. The diagnosis and differentiation, etc. of bleeding and calcification of multiple sclerosis and Alzheimer's disease becomes possible by a susceptibility map which maps the susceptibility of the tissue.

However, artifacts and noise can be generated in the susceptibility map or the conductivity map that quantified the electromagnetic properties of the tissue by a difference in the linearity model.

DETAILED DESCRIPTION

According to one embodiment, a magnetic resonance imaging apparatus includes processing circuitry. The processing circuitry generates a conductivity map quantitatively indicating the conductivity in the subject using a susceptibility map quantitatively indicating the susceptibility in the subject.

The purpose is to realize high image quality and noise reduction of the image in which the electromagnetic properties of the tissue were quantified.

The magnetic resonance imaging apparatus according to the present embodiment will be described with reference to the accompanying drawings. In the description below, structural elements having substantially the same functions and configurations will be denoted by the same reference symbols, and a repetitive description of such elements will be given only where necessary.

Figure 1:
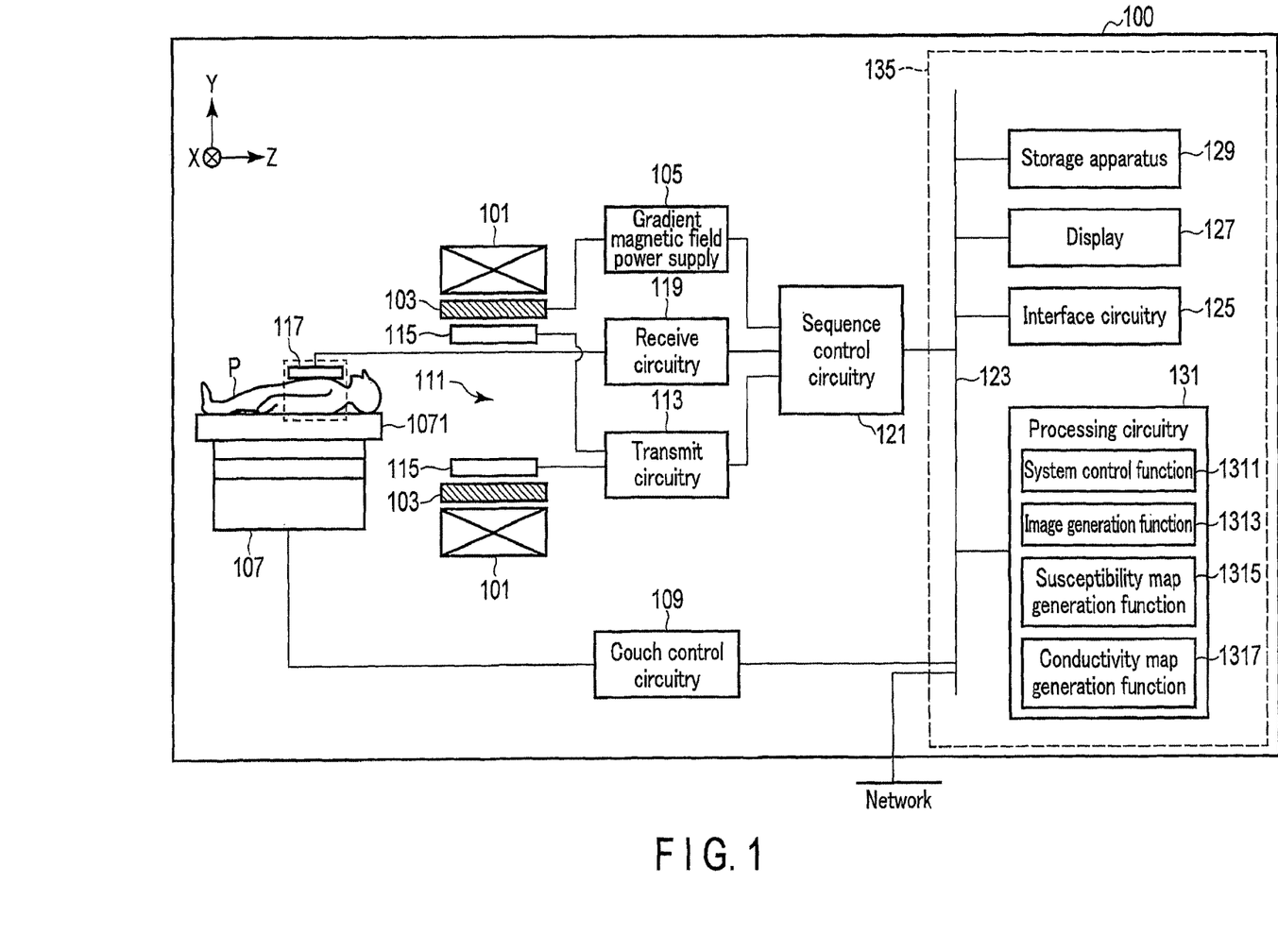
FIG. 1 is a diagram showing the configuration of the MRI apparatus 100 according to the embodiment.

The configuration of a magnetic resonance imaging (MRI) apparatus according to the present embodiment will be described with reference to FIG. 1. FIG. 1 is a diagram showing the configuration of the MRI apparatus 100 according to the present embodiment. As shown in FIG. 1, the MRI apparatus 100 of the present embodiment includes a static field magnet 101, a gradient coil 103, a gradient magnetic field power supply 105, a couch 107, a couch control circuitry 109, a transmit circuitry (transmitter) 113, a transmitter coil 115, a receiver coil 117, a receive circuitry (receiver) 119, a sequence control circuitry (collection unit) 121, a bus 123, an interface circuitry (input unit) 125, a display (display unit) 127, a storage apparatus (storage unit) 129, and a processing circuitry (processor) 131. The MRI apparatus 100 may have a hollow cylindrical-shaped shim coil provided between the static field magnet 101 and the gradient coil 103.

The static magnetic field magnet 101 is a magnet formed in a hollow, approximately cylindrical shape. The static magnetic field magnet 101 is not necessarily in an approximately cylindrical shape; it may be formed in an open shape. The static magnetic field magnet 101 generates a uniform static magnetic field $B_0$ in its inner space. As the static magnetic field magnet 101, for example, a superconductive magnetic is used.

The gradient coil 103 is a coil formed in a hollow cylindrical shape. The gradient coil 103 is disposed inside the static magnetic field magnet 101. The gradient coil 103 is formed by combining three coils respectively corresponding to the X-, Y-, and Z-axes which are orthogonal to each other. The Z-axis direction is defined as the same direction of the static magnetic field $B_0$. In addition, a Y-axis direction is a vertical direction, and an X-axis direction is a direction perpendicular to each of the Z-axis and the Y-axis. These three coils in the gradient coil 103 are separately supplied with a current from the gradient magnetic field power supply 105 and respectively generate gradient magnetic fields in which magnetic field intensity changes along each of the X-, Y-, and Z-axes.

Herein, the gradient magnetic fields of the X-, Y, and Z-axes that are generated by the gradient coil 103 respectively correspond to, for example, a gradient magnetic field for slice selection, a gradient magnetic field for phase encoding, and a gradient magnetic field for frequency encoding (also referred to as a readout gradient magnetic field).

The gradient magnetic field for slice selection is used to desirably determine an imaging slice. The gradient magnetic field for phase encoding is used to change a phase of a magnetic resonance (MR) signal in accordance with a spatial position. The gradient magnetic field for frequency encoding is used to change a frequency of a MR signal in accordance with a spatial position.

The gradient magnetic field power supply 105 is a power supply apparatus that supplies a current to the gradient coil 103 under the control of the sequence control circuitry 121.

The couch 107 is an apparatus having the couch top 1071 on which a subject P is laid. The couch 107 inserts the couch top 1071 on which the subject P is laid into the bore 111 under the control of the couch control circuitry 109. Normally, the couch 107 is installed in an examination room where the MRI apparatus 100 is installed, in such a manner that the longitudinal axis of the couch 107 is parallel to the central axis of the static field magnet 101.

The couch control circuitry 109 is circuitry for controlling the couch 107, and is implemented by a processor, for example. The couch control circuitry 109 drives the couch 107 in accordance with an operator's instruction via the interface circuitry 125 to move in a couch top 1071 in a longitudinal direction and a vertical direction.

The transmit circuitry 113 supplies, by the control of the sequence control circuitry 121, a high-frequency pulse, corresponding to a Larmor frequency, to the transmit coil 115.

The transmit coil 115 is a radio frequency (RF) coil located inside the gradient coil 103. Upon being supplied with a high-frequency pulse (RF pulse) from the transmit circuitry 113, the transmit coil 115 generates a transmit RF wave that is equivalent to a high-frequency magnetic field. The transmit coil is, for example, a whole body (WB) coil. The WB coil may be used as a transmit/receive coil.

The receive coil 117 is a radio frequency (RF) coil located inside the gradient coil 103. The receive coil 117 receives a MR signal that is emitted from the subject P by a high-frequency magnetic field. The receive coil 117 outputs the received MR signal to the receive circuitry 119. The receive coil 117 is, for example, a coil array having one or more elements, typically a number of coil elements. In FIG. 1, the transmit coil 115 and the receive coil 117 are illustrated as separate RF coils; however, the transmit coil 115 and the receive coil 117 may be realized by an integrated transmit/receive coil. The transmit/receive coil is, for example, a local transmit/receive RF coil, such as a head coil, to serve an imaging target in a subject P.

The receive circuitry 119 generates, under the control of the sequence control circuitry 121, a digital MR signal, which is digitized complex number data, based on the MR signal that is output from the receive coil 117. Specifically, the receive circuitry 119 performs various types of signal processing to the MR signal that is output from the receive coil 117, and then performs analog-to-digital (A/D) conversion of data to which the variety of signal processing is performed. The receive circuitry 119 performs sampling to the A/D converted data. By this processing, the receive circuitry 119 generates a digital MR signal (hereinafter referred to as magnetic resonance (MR) data). The receive circuitry 119 outputs the generated MR data to the sequence control circuitry 121.

The sequence control circuitry 121 controls the gradient magnetic field power supply 105, the transmit circuitry 113, and the receive circuitry 119 etc. in accordance with an imaging protocol that is output from the processing circuitry 131, and performs imaging on the subject P. An imaging protocol has different pulse sequences in accordance with a type of examination. In an imaging protocol, defined are a value of a current supplied to the gradient coil 103 by the gradient magnetic field power supply 105, timing of supplying a current to the gradient coil 103 by the gradient magnetic field power supply 105, a magnitude of an RF pulse supplied to the transmit coil 115 by the transmit circuitry 113, timing of supplying an RF pulse to the transmit coil 115 by the transmit circuitry 113, timing of receiving an MR signal by the receive circuitry 117, and the like. An amplitude of a current supplied to the gradient coil 103 from the gradient magnetic field power supply 105 corresponds to a waveform of a readout gradient magnetic field in accordance with a pulse sequence.

The bus 123 is a transmit path for transmitting data among the interface circuitry 125, the display 127, the storage apparatus 129, and the processing circuitry 131. The bus 123 may be connected to various types of biosignal measuring instruments, external storage devices and various modalities through a network, etc.

The interface circuitry 125 is circuitry for receiving various instructions and information that are input from an operator. The interface circuitry 125 is circuitry for a pointing device, such as a mouse, or for an input device, such as a keyboard, etc. The interface circuitry 125 is not limited to circuitry for physical operation members such as a mouse and a keyboard. The interface circuitry 125 also includes, for example, electric signal processing circuitry that receives an electric signal corresponding to an input operation through an external input device provided separately from the present MRI apparatus 100 and outputs the received electric signal to different circuitry.

The display 127, under the control by the system control function 1311 in a processing circuitry 131, for example, displays various images and information such as a MR image reconstructed by an image generation function 1313, a susceptibility map generated by the susceptibility map generation function 1315 and a conductivity map, etc. generated by the conductivity map generation function 1317. The susceptibility map is an image quantitatively indicating a plurality of susceptibility in the subject and the conductivity map is an image quantitatively indicating a plurality of conductivity in the subject. The display 127 is, for example, a CRT display, a liquid crystal display, an organic EL display, an LED display, a plasma display, a monitor, or any other display known in this technical field.

The storage apparatus 129 stores MR data filled in k-space by the image generation function 1313, and image data etc. generated by the image generation function 1313. The storage apparatus 129 stores various types of imaging protocols, conditions for imaging etc., including a plurality of imaging parameters that define imaging protocols. The storage apparatus 129 stores programs corresponding to various functions executed by the processing circuitry 131. The storage apparatus 129 is for example, a RAM (Random Access Memory), semiconductor memory element, such as flash memory, etc., hard disk drive, solid state drive, and optical disc, etc. The storage apparatus 129 may be a drive apparatus, etc. configured to read and write various kinds of information with respect to a portable storage medium such as a CD-ROM drive, a DVD drive, or a flash memory, etc.

The processing circuitry 131 includes a processor (not-shown in the drawings), and a memory, such as a ROM or a RAM, as hardware resources, to control the MRI apparatus 100 integrally. The processing circuitry 131 includes a system control function 1311, an image generation function 1313, a susceptibility map generation function 1315, and a conductivity map generation function 1317. The various functions, which are performed by the system control function 1311, the image generation function 1313, the susceptibility map generation function 1315, and the conductivity map generation function 1317, are stored in the storage apparatus 129 in a form of a computer-executable program. The processing circuitry 131 is a processor that reads from the storage apparatus 129 a program corresponding to each function, and executes the program to realize the function corresponding to each program. In other words, the processing circuitry 131, in a state where each of the programs is read, has a plurality of the functions etc. shown in the processing circuitry 131 of FIG. 1.

FIG. 1 illustrates that the various functions are realized by single processing circuitry 131; however, the processing circuitry 131 may include a plurality of independent processors, and the functions may be realized by each of the processors executing respective programs. In other words, there may be a case where each of the aforementioned functions may be configured as a program, and single processing circuitry executes each program or a case where specific functions may be implemented in independent program-execution circuitry that is specific to respective functions. The system control function 1311, the image generation function 1313, the susceptibility map generation function 1315, and the conductivity map generation function 1317 of the processing circuitry 131 are examples of a system controller, an image generator, a susceptibility map generation unit, and a conductive map generation unit, respectively.

The term "processor" used in the above description means, for example, a CPU (Central Processing Unit), a GPU (Graphical Processing Unit), or circuitry such as an ASIC (Application Specific Integrated Circuit), or a programmable logic device (e.g. SPLD (Simple Programmable Logic Device), CPLD (Complex Programmable Logic Device), or a FPGA (Field Programmable Gate Array)).

The processor reads and executes a program stored in the storage apparatus 129 to realize the corresponding function. A program may be directly integrated into the circuitry of the processor, instead of storing the program on the storage apparatus 129. In this case, the function is realized by reading and executing the program integrated into the circuitry. Similarly, each of the couch control circuitry 109, the transmit circuitry 113, the receive circuitry 119, and the sequence control circuitry 121, etc. are also configured as an electronic circuit, such as the above processor.

The processing circuitry 131 integrally controls the MRI apparatus 100 by the system control function 1311. Specifically, the processing circuitry 131 reads a system control program stored in the storage apparatus 129 and expands it in the memory, and controls each circuitry of the MRI apparatus 100 in accordance with the expanded system control program. For example, by the system control function 1311, the processing circuitry 131 reads an imaging protocol from the storage apparatus 129 based on conditions for imaging that are input by an operator through the interface circuitry 125. The processing circuitry 131 may also generate an imaging protocol based on conditions for imaging. The processing circuitry 131 transmits the imaging protocol to the sequence control circuitry 121 to control imaging of the subject P.

The processing circuitry 131 fills the MR data along a readout direction of k-space in accordance with a strength of the readout gradient magnetic field by the image generation function 1313. The processing circuitry 131 generates the MR image by executing a Fourier transform to the MR data filled in the k-space. For example, the processing circuitry 131 generates a real image based on real data of the MR data. The processing circuitry 131 generates an imaginary image based on imaginary data of the MR data. The processing circuitry 131 generates a magnitude image using magnitude (absolute value) of the real image and magnitude (absolute value) of the imaginary image. The processing circuitry 131 generates a phase image by calculating arc tangent ($\tan^{-1}$) to a ratio of real image to imaginary image. The processing circuitry 131 outputs an MR image such as magnitude image and phase image to the display 127 and the storage apparatus 129. The susceptibility map generation function 1315 and the conductivity map generation function 1317 that are realized by the processing circuitry 131 will be described later in detail.

The overall configuration of the MRI apparatus 100 according to the present embodiment has been described above. Prior to the explanation of the susceptibility map generation function 1315 and the conductivity map generation function 1317, the following explains the collection of MR data concerning phase image used in the generation of the susceptibility map. Next, the generation of the susceptibility map and the generation of the conductivity map will be described.

The sequence control circuitry 121 scans the subject P in accordance with an imaging protocol having a gradient echo pulse sequence. Specifically, the imagining protocol has a pulse sequence using multi-echo method in a gradient echo type or a pulse sequence using EPI (Echo Planar Imaging) in a gradient echo type. By such structure, the sequence control circuitry 121 collects MR data with different echo times.

The processing circuitry 131 generates a plurality of phase images each corresponding to a plurality of echo times using MR data with different echo times by the image generation function 1313. Each pixel of the plurality of phase images are allocated with a phase value (spin phase information) of a range (hereinafter referred to as a phase range) of a $-\pi$ radian (rad) to $+\pi$ radian (rad). In other words, the phase value below $-\pi$ radian and the phase value over $+\pi$ radian are wrapped in its phase range when generating a phase image.

The processing circuitry 131 calculates a susceptibility value based on spin phase information in MR data and generates a susceptibility map by the susceptibility map generation function 1315. Specifically, the processing circuitry 131 generates a susceptibility map by a nonlinear processing to the phase information. The processing circuitry 131 executes the nonlinear processing to each of the plurality of phase images and calculates the susceptibility value. The nonlinear processing is for example, phase-wrapping removal, background field removal (static magnetic field $B_0$), susceptibility calculation processing, etc. for calculating the susceptibility value from a plurality of phase images (hereinafter referred to as a tissue phase image) that has been treated with the above removal processing. The phase-wrapping removal and the background field removal, which are nonlinear high image quality processing of the non-linear processing, can be performed by the image generation function 1313. The following explains matters regarding the nonlinear processing.

The processing circuitry 131 executes phase-wrapping removal to each of the plurality of phase images by the susceptibility map generation function 1315. More specifically, the processing circuitry 131 executes phase-wrapping removal using a publicly-known method, for example, a region expansion method, Laplacian method, graph cut method, etc. used in the technical field of MRI and the technical field of SAR (Synthetic Aperture Radar). The phase image after phase-wrapping removal superimposes a phase originating in the susceptibility of the body tissues, and the phase originating in the influence of background magnetic field. The phase originating in the influence of a background magnetic field is larger than the phase originating in the susceptibility of the body tissue for about 10 times or more. In order to improve the accuracy of the susceptibility of the body tissue, a processing of removing the phase originating in the influence of the background magnetic field from the phase image removed with phase wrapping, in other words, background field removal, becomes necessary.

The processing circuitry 131 executes background field removal to the phase image removed with phase wrapping by the susceptibility map generation function 1315. Specifically, the processing circuitry 131 uses various methods such as a method of applying a filter, a SHARP (Sophisticated Harmonic Artifact Reduction on Phase data) method (includes improved SHARP method and RESHARP (Regularization-Enabled SHARP) method), or a PDF (Projection onto Dipole Field) method to remove the influence of the background magnetic field. The processing circuitry 131, by performing any of the above background effect removal methods to a phase image after phase wrapping, generates a tissue phase image where the influence of the background magnetic field is removed.

Figure 2:
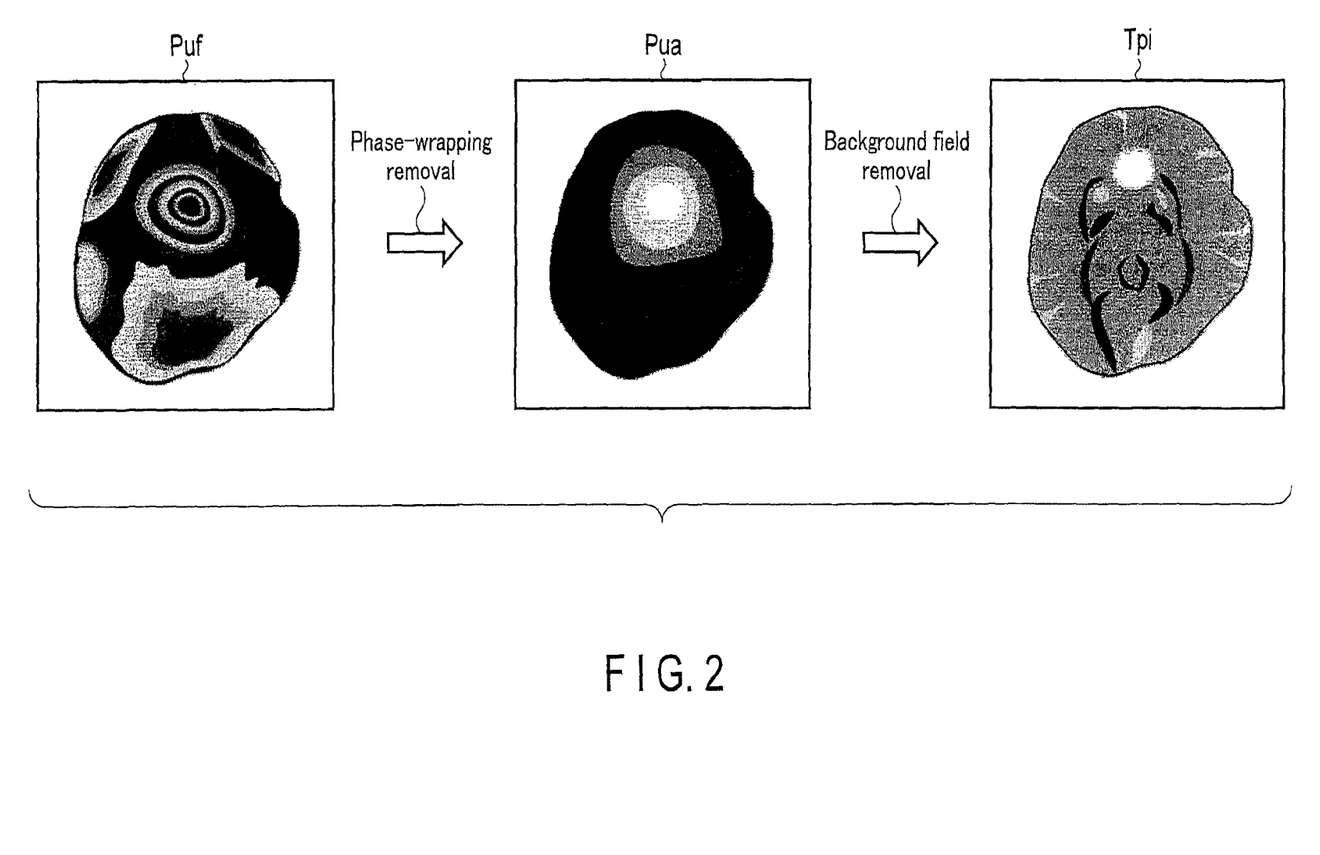
FIG. 2 is a diagram showing an example of tissue phase image performed with phase-wrapping removal and background field removal according to the embodiment.

FIG. 2 is a diagram showing an example of a tissue phase image performed with phase-wrapping removal and background field removal according to the embodiment. The phase image Puf before the phase-wrapping removal in FIG. 2 indicates a phase image generated by the image generation function 1313. The gradation of the phase image Puf indicates a phase value in the phase range of $-\pi$ radian to $+\pi$ radian. The gradation of the phase image Pua after the phase removal in FIG. 2 indicates the phase value in the phase range of, for example, $-3\pi$ radian to $+3$ radian. The phase image Tpi after background field removal in FIG. 2 indicates a tissue phase image. The processing circuitry 131 generates, by the susceptibility map generating function 1315, a plurality of tissue phase images corresponding to a plurality of echo times.

The processing circuitry 131 executes, by the susceptibility map generation function 1315, a regression analysis to a distribution of the phase value to the echo time (hereinafter referred to as a phase distribution) for each of the plurality of pixels of the same position in the plurality of tissue phase images. In other words, the processing circuitry 131 executes fitting by such regression analysis. The processing circuitry 131 determines by regression analysis, for every pixel, a regression parameter such as a result of the regression analysis, for example, inclination of the regression line in a phase distribution. The regression analysis is not limited to linear regression analysis, for example, robust estimation or regularization regression, nonlinear regression (machine learning such as support vector machine or random forest), and various complex regression analysis can be used. The processing circuitry 131 calculates the susceptibility value per pixel by executing a susceptibility calculation processing to a determined inclination.

Specifically, the regression line as a result of the regression analysis can be represented as $$\varphi = a \times TE + \varphi_0 \quad (1)$$

when $\varphi$ is phase value, a is inclination, TE is echo time, and $\varphi_0$ is intercept (initial phase value). The inclination a can be represented as a product of a proton gyromagnetic ratio $\gamma$, a static magnetic field $B_0$, and a magnetic field distribution $\delta$.

$$a = \gamma \times B_0 \times \delta \quad (2)$$

The magnetic field distribution $\delta$ is also called a local field map and is equivalent to a relative magnetic field change caused by the difference in susceptibility values of the body tissues. In other words, the magnetic field distribution $\delta$ is when the magnetic field generated by the susceptibility in each of the plurality of pixels of the tissue phase image indicates a distribution of a magnetic field that affects each of the pixels in the tissue phase image.

The processing circuitry 131 calculates the magnetic field distribution $\delta$ by dividing the determined inclination with a product (Larmour frequency $\omega$) of the gyromagnetic ratio $\gamma$ and the static magnetic field $B_0$ by the susceptibility map generation function 1315. For the calculated magnetic field distribution $\delta$, the processing circuitry 131 calculates the susceptibility value of each pixel by executing various suitable methods of such as for example, L1 Norm regularization etc. The following describes the processing for calculating the susceptibility value from the magnetic field distribution $\delta$.

The magnetic field distribution $\delta$ is represented in the following by the convolutional integration ($\delta = d * \chi$) between dipole kernel d and the value of magnetic susceptibility $\chi$ (susceptibility value).

$$\delta = d * \chi \quad (3)$$

When the Fourier transform F is executed to both sides of equation (3), the equation (3) will become the following equation (4).

$$F[\delta] = D \times F[\chi] \quad (4)$$

D in equation (4) is the Fourier transform (D=F[d]) of d in the dipole kernel and is represented by the following.

$$D = 1/3 - k_z^2/(k_x^2 + k_y^2 + k_z^2) \quad (5)$$

In equation (5), the reciprocal $D^{-1}$ of D is zero when $k_z^2/(k_x^2 + k_y^2 + k_z^2) = 1/3$. Therefore, the method of obtaining F[x] by multiplying the reciprocal $D^{-1}$ of D from the left-hand side to both sides of equation (4) will be an ill-posed problem.

In order to solve the above ill-posed problem, for example, the L1 norm regularization process is used. First, when the inverse Fourier transform is executed to both sides of equation (4), the following equation (6) is obtained.

$$\delta = F^{-1}[D \times F[\chi]] \quad (6)$$

The first evaluation function $f_1(\chi)$ for estimating the susceptibility value is, for example, set as shown in the following equation (7) by using the left-hand side ($\delta - F^{-1}[D \times F[\chi]]$) when the right-hand side of equation (6) is shifted to the left-hand side and the spatial smoothness of the susceptibility value and regularization term of the edge structure etc.

$$f_1(\chi) = \|W_1 \times (\delta - F^{-1}[D \times f[\chi]])\|_2^2 + \lambda \|\chi\|_1 \quad (7)$$

The first term of the right-hand side in equation (7) is a secondary norm squared indicating the degree of match of equation (6). The second term of the right-hand side of equation (7) is a regularization term. In addition, the $\lambda$ in the second term of the right-hand side of equation (7) is a parameter concerning regularization term (regularization parameter). The $W_1$ of the first term of the right-hand side of equation (7) is a weighting coefficient that is equivalent to the reliability of each pixel. As the weighting coefficient, for example, noise amount (variance) of the magnitude image corresponding to the phase image, non-uniformity of the static magnetic field, etc. is used.

The processing circuitry 131 calculates the susceptibility value for each pixel by a first optimization processing for minimizing the right-hand side of equation (7) by the susceptibility map generation function 1315. As a method of stably obtaining an approximate susceptibility value in equation (7), the processing circuitry 131 calculates the susceptibility value using various optimization processes of, for example, Newton's method, steepest descent method, conjugate gradient method, nonlinear conjugate gradient method, penalty method, or ADMM (Alternating Direction Method of Multipliers), etc. The processing circuitry 131 generates a Quantitative Susceptibility Mapping (QSM) by mapping the susceptibility value for each calculated pixel on a corresponding pixel. Furthermore, the processing circuitry 131 can generate a graph showing the susceptibility value corresponding to the coordinate positions of each image. The processing circuitry 131 can generate a new image by multiplying or dividing the pixel value or the like in the magnitude image by the pixel image of the tissue phase image or susceptibility value of the susceptibility map. The processing circuitry 131 can colorize the susceptibility map and generate an image superimposed on the gray scale magnitude image (susceptibility superimposed image).

The processing circuitry 131 calculates the conductivity value in the subject using a susceptibility value in the susceptibility map, and generates a conductivity map using the calculated conductivity value by the conductivity map generation function 1317. The processing circuitry 131 generates a conductivity map by order transforming the susceptibility map in accordance with Maxwell's equations. The susceptibility map used for generation of the conductivity map is a susceptibility map generated by the susceptibility map generation function 1315. In this case, the processing circuitry 131 calculates the conductivity value using a susceptibility value calculated by the susceptibility map generation function 1315.

The susceptibility map used for the generation of the conductivity map is not limited to a susceptibility map generated by the susceptibility map generation function 1315, and can be, for example, a susceptibility map actually measured by the susceptometer, etc., or can be a susceptibility map generated in the past using a nonlinear high-quality processing. The processing circuitry 131 reads a susceptibility map used to generate a conductivity map from a storage apparatus 129, or through a network.

Specifically, the processing circuitry 131, by the conductivity map generation function 1317, converts (hereinafter referred to as order transformation) the susceptibility value in the susceptibility map to a result of regression analysis in phase distribution, for example, to a new inclination a' of the regression line by using an effect relation (equation (1), equation (2), equation (5), equation (6) etc.) to the phase values by the echo times TE and the susceptibility value. The processing circuitry 131 updates the inclination a in equation (1) to an order transformed inclination a'. The processing circuitry 131 specifies a phase value $\varphi_0$ (hereinafter referred to as initial phase value) at a point when the echo time TE is zero by a further regression analysis using the phase distribution and the updated inclination a'.

The processing circuitry 131 calculates the conductivity value using the initial phase value $\varphi_0$ specified by the conductivity map generation function 1317. Specifically, the processing circuitry 131 calculates the conductivity value using the following relation equation (8) between the following initial phase value $\varphi_0$ and the value (conductivity value) of conductivity $\sigma$.

$$\sigma = \nabla^2 \varphi_0 / (\omega \times \mu_0) \qquad (8)$$

The operator $\nabla^2$ of the right-hand side of equation (8) is nabla squared and is equivalent to a Laplacian. The $\mu_0$ of right-hand side of equation (8) is a vacuum magnetic permeability. The Laplacian in equation (8) is a second order differential; and therefore, is equivalent to a high-pass filter. The calculation result of $\nabla^2 \varphi_0$ will emphasize the noise component included in the initial phase value $\varphi_0$.

The second evaluation function $f_2(\sigma)$ for estimating conductivity value using equation (8) without emphasizing the noise is set for example, as shown in the following equation (9) based on the method for minimizing the mean square error (MSE).

$$f_2(\sigma) = \|\sigma - \nabla^2 \varphi_0 / (\omega \times \mu_0)\|_2^2 \qquad (9)$$

The right-hand side in equation (9) is a secondary norm squared indicating the degree of match of the equation (8).

The processing circuitry 131 calculates the conductivity value for each pixel by a secondary optimization processing for minimizing the right-hand side of equation (9) by the conductivity map generation function 1317. The processing circuitry 131 calculates the conductivity value by minimizing the right-hand side of equation (9) using, for example, various optimization methods similar to the first optimization processing. The processing circuitry 131 generates a Quantitative Conductivity Mapping (QCM) by mapping the conductivity value for each calculated pixel on a corresponding pixel. Furthermore, the processing circuitry 131 can generate a graph showing the conductivity value corresponding to the coordinate positions of each image. The processing circuitry 131 can generate a new image by multiplying or dividing the pixel value or the like of the magnitude image by the conductivity value of the conductivity map. The processing circuitry 131 can colorize the conductivity map and generate an image superimposed on the gray scale magnitude image (conductivity superimposed image).

The evaluation function $f_2(\sigma)$ can be set as shown in the following equation (10) using a weighting coefficient $W_2$ that is equivalent to the reliability per pixel.

$$f_2(\sigma) = W_2 \times \|\sigma - \nabla^2 \varphi_0 / (\omega \times \mu_0)\|_2^2 \qquad (10)$$

The $W_2$ on the right-hand side of equation (10) uses for example, a noise amount (variance) of a magnitude image corresponding to a phase image, a non-uniformity of the static magnetic field, and a noise amount (variance) of the susceptibility map or the like. The second optimization processing used in equation (10) is equivalent to a weighted optimization processing using the noise amount of a magnitude image, the non-uniformity of the static magnetic field, or the noise amount of susceptibility map as weights.

The evaluation function $f_2(\sigma)$ can be set as shown in the following equation (11) by adding the regularization item to equation (10).

$$f_2(\sigma) = W_2 \times \|\sigma - \nabla^2 \varphi_0 / (\omega \times \mu_0)\|_2^2 + \lambda \|I(\sigma, \chi)\|_1 \qquad (11)$$

The $I(\sigma, \chi)$ in the second item on the right-hand side of equation (11) is equivalent to degree of similarity between the susceptibility map and the conductivity map. The second optimization processing using equation (11) is equivalent to the optimization processing using the structural degree of similarity between the susceptibility map and conductivity map as a regularization parameter. In the second optimization processing using equation (11), for each of the repeat operator for minimizing $f_2(\sigma)$, the processing circuitry 131 generates a conductivity map, and calculates the degree of similarity with the generated conductivity map and susceptibility map. The processing circuitry 131 calculates the degree of similarity $I(\sigma,\chi)$ by using, for example, a correlation function, the mutual information content, etc. between the conductivity map and susceptibility map.

(Operation)

Figure 3:
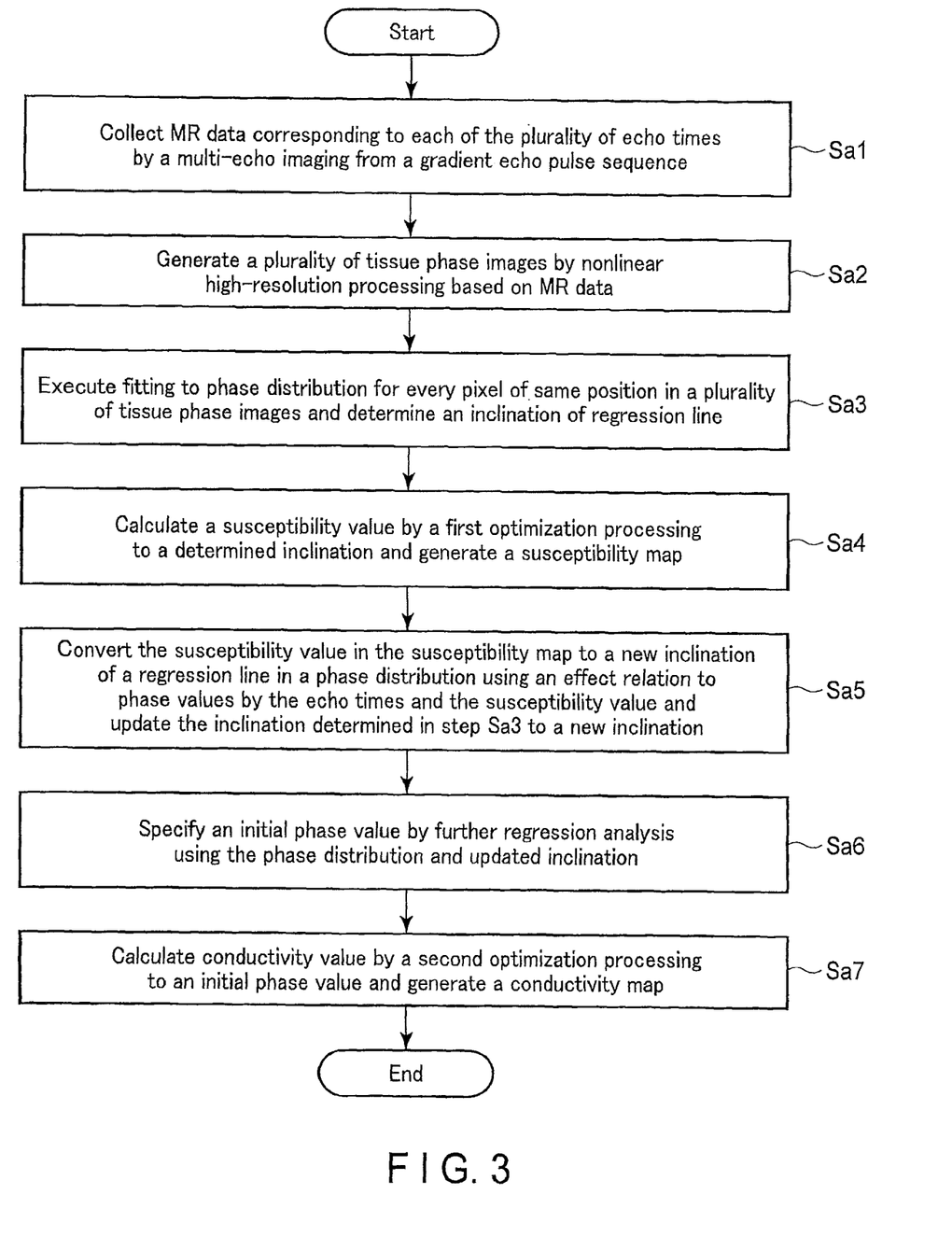
FIG. 3 is a flowchart showing an example of a processing of an operation according to the embodiment.

FIG. 3 is a flowchart showing an example of a process of an operation according to the embodiment.

(Step Sa1)

An imaging protocol having a gradient echo pulse sequence is read from the storage apparatus 129. In order to simplify the following explanation, the gradient echo pulse sequence is a multi-echo method and there are four different echo times. By executing the read imaging protocol, the multi-echo imaging is performed to the subject P. The MR data corresponding to each of the plurality of echo times TE is collected by the multi-echo imaging.

(Step Sa2)

A plurality of phase images in accordance with the echo times TE are generated based on the MR data. Phase-wrapping removal, which is a nonlinear high quality processing of the nonlinear processing, and background field removal are executed for each of the generated plurality of phase images, and a plurality of tissue phase images in accordance with the echo times are generated.

Also, when the noise amount of the magnitude image is used in calculation of the susceptibility value and/or the conductivity value, the plurality of magnitude images in accordance with the echo times TE are generated by the image generation function 1313 in the processing circuitry 131. Next, the variance of the magnitude image is calculated by the image generation function 1313 as the noise amount using a plurality of pixel values in at least one of the generated plurality of magnitude images.

(Step Sa3)

The regression parameter is determined by a regression analysis to the phase distribution for each pixel in the same position in the plurality of tissue phase images. For example, the fitting is executed by the regression analysis. By such fitting, the inclination a (regression parameter) of the regression line in equation (1) is determined for each pixel.

Figure 4:
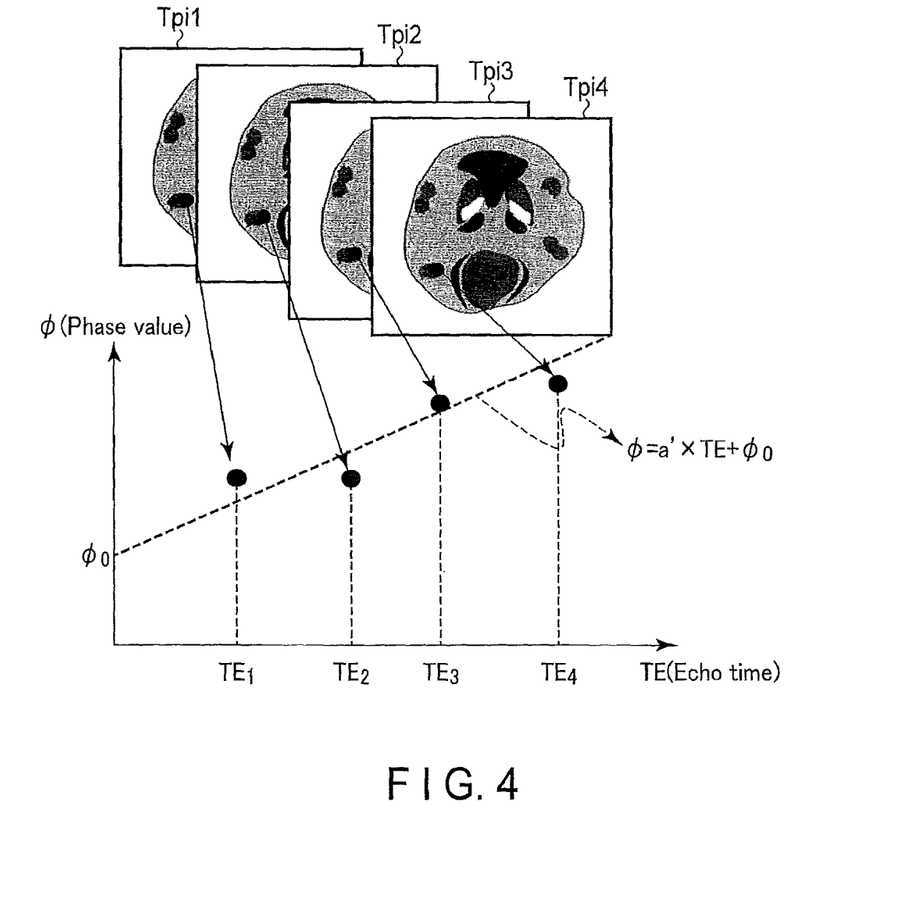
FIG. 4 is a diagram showing an example of fitting to a phase distribution for each pixel of a same position in a plurality of tissue phase images having different echo times according to the embodiment.

FIG. 4 is a diagram showing an example of fitting to a phase distribution for each pixel of a same position in a plurality of tissue phase images having different echo times. The graph of FIG. 4 shows the phase distribution for each pixel in the same position and an example of fitting of equation (1) in a tissue phase image Tpi1 corresponding to echo time $TE_1$, a tissue phase image Tpi2 corresponding to echo time $TE_2$, a tissue phase image Tpi3 corresponding to echo time $TE_3$ and a tissue phase image Tpi4 corresponding to echo time $TE_4$.

(Step Sa4)

The susceptibility value is calculated for each pixel by the first optimization processing of the results of regression analysis. Specifically, the susceptibility value is calculated for each pixel by the first optimization processing to the magnetic field distribution $\delta$ in a determined inclination. The susceptibility map is generated using a plurality of susceptibility values each corresponding to a plurality of pixels. When the noise amount of the susceptibility map in the second optimization processing is used, the variance of the susceptibility map is calculated by the susceptibility map generation function 1315 as a noise amount. The processing in step Sa2 and step Sa4 is equivalent to a nonlinear processing to the plurality of phase images each corresponding to a plurality of echo times TE.

When the high-resolution susceptibility map with noise or artifacts reduced by the nonlinear processing etc., or the susceptibility map actually measured by the susceptometer, etc. is stored in the storage apparatus 129, the processings of step Sa2 to step Sa4 becomes unnecessary. In that case, the processing of following step Sa5 is executed by using the susceptibility map read from the storage apparatus 129.

(Step Sa5)

The susceptibility value in the susceptibility map converts, when using the effect relation (equation (1), equation (2), equation (5), and equation (6) etc.) to a phase value by the echo time TE and susceptibility value, to a new regression parameter in the phase distribution. In other words, the susceptibility value in the susceptibility map converts to a new inclination a' of the regression line in phase distribution by order transformation using an effect relation. Specifically, the Fourier transform $F[\chi]$ of magnetic susceptibility $\chi$ in the susceptibility map is calculated by the conductivity map generation function 1317 in the processing circuitry 131. As shown in equation (6), the inverse Fourier transform is executed on the product of the Fourier transform $F[\chi]$ of the magnetic susceptibility $\chi$ and the Fourier transform D of the dipole kernel d shown in equation (5). A new magnetic field distribution $\delta'$ is calculated by such inverse Fourier transform. As shown in equation (2), a new inclination a' is calculated by multiplying gyromagnetic ratio $\gamma$ of the proton and static magnetic field $B_0$ to a new magnetic field distribution $\delta'$. That is, the susceptibility map converts to new inclination a' by order transformation using equation (1), equation (2), equation (5), and equation (6). Next, the inclination a determined by step Sa3 is updated to converted inclination a'. This update in inclination is equivalent to inclination a of regression line in FIG. 4 being changed to inclination a' converted by order transformation of the susceptibility value. In other words, the regression parameter a is updated to new regression parameter a'.

Further, when the susceptibility map used in the generation of a susceptibility map through the storage apparatus 129 or the network is read, the susceptibility map is converted to the inclination by order transformation in the conductivity map generation function 1317. The process of the hereinafter described step Sa6 is executed using a converted inclination.

(Step Sa6)

By further regression analysis using phase distribution and updated regression parameter, the initial phase value $\varphi_0$ where echo time TE is zero is specified. For example, the initial phase value $\varphi_0$ is specified by further regression analysis using phase distribution and updated inclination. Specifically, by the line of inclination a' being translated along the axis indicating the phase value in the phase distribution and applying the least squares method to the phase distribution, the initial phase value is $\varphi_0$ specified.

(Step Sa7)

The conductivity value is calculated for each pixel by the second optimization processing to the specified phase value. The conductivity map is generated using a plurality of conductivity values each corresponding to a plurality of pixels. As shown in FIG. 4, in the regression parameter determined by a further regression analysis executed in the processing of step Sa5 and step Sa6, the inclination a' of the regression line corresponds to the susceptibility map and the initial phase value $\varphi_0$ corresponds to the conductivity map.

Figure 5:
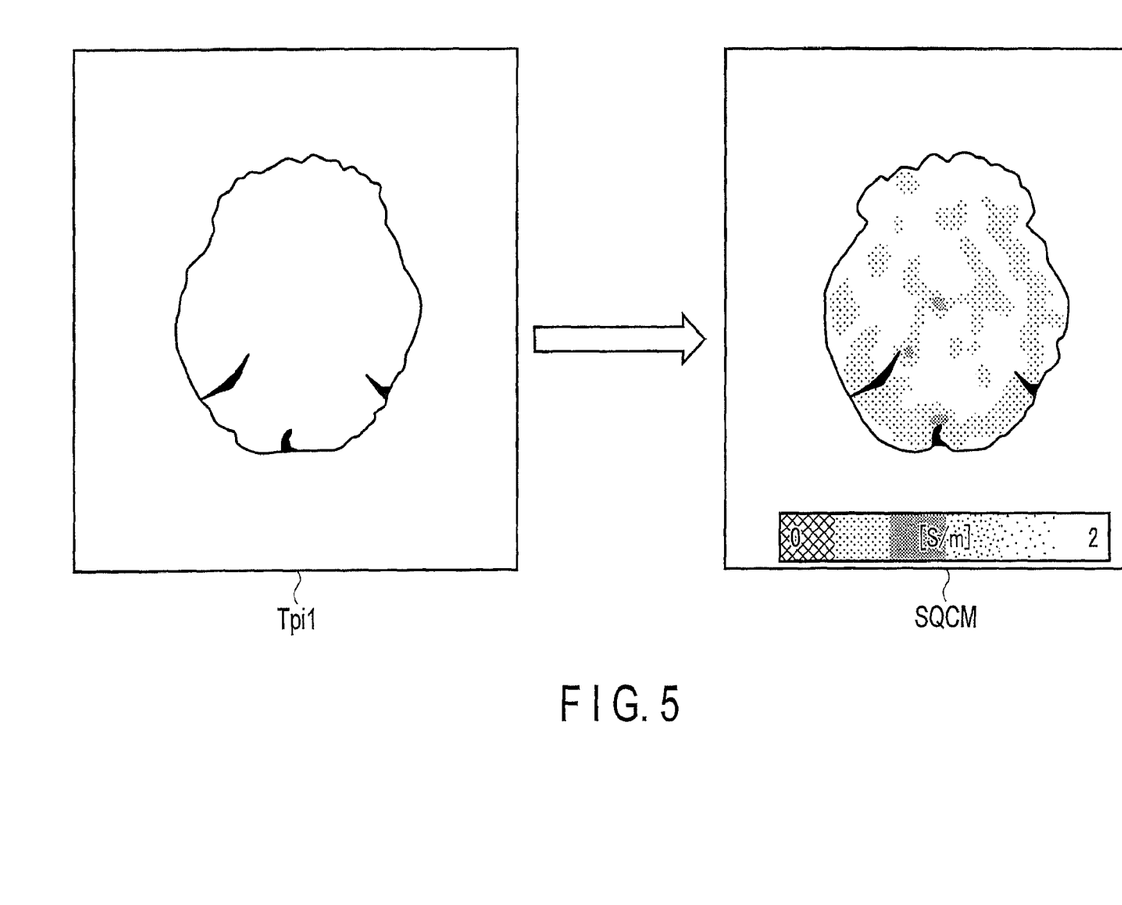
FIG. 5 is a diagram showing an example of tissue phase image Tpi1 corresponding to echo time $TE_1$ and conductivity superimposed image SQCM according to the embodiment.

FIG. 5 is a diagram showing an example of tissue phase image Tpi1 corresponding to echo time $TE_1$ and conductivity superimposed image SQCM. As shown in FIG. 5, the conductivity superimposed image SQCM reduces the artifacts and noise and displays to display 127.

According to the above-described configuration, the following advantageous effects can be obtained.

According to the MRI apparatus 100 of the present embodiment, the conductivity value in the subject is calculated using the susceptibility value in the susceptibility map quantitatively indicating the plurality of susceptibility in the subject, and generated a conductivity map quantitatively indicating the plurality of conductivity in the subject using a conductivity value. Specifically, according to the present MRI apparatus 100, the magnetic resonance data with different echo times are collected by imaging the subject P using a gradient echo pulse sequence, the susceptibility value is calculated by the nonlinear processing to the phase information based on a spin phase information in the magnetic resonance data, the susceptibility map is generated using calculated susceptibility value, and the conductivity value is calculated using the calculated susceptibility value. More specifically, according to the present MRI apparatus 100, converting (updating) the susceptibility value to a regression parameter (inclination of the regression line) in the distribution of the phase value to the echo time for each pixel by using the effect relation to a phase information (spin phase information) by the echo time and the susceptibility value, specifying the phase value when the echo time is zero by the regression using the converted (updated) inclination and phase distribution, and calculating the conductivity value using the specified phase value can be achieved.

Furthermore, according to the MRI apparatus 100, the noise amount of the susceptibility map is calculated based on the susceptibility value in the susceptibility map, and the conductivity value is calculated by the weight optimization processing that uses the calculated noise amount as a weight. According to the present MRI apparatus 100, the susceptibility map is generated by removing non-uniformity of the static magnetic field $B_0$ in the imaging to subject P from the phase information, and the conductivity value is calculated by weight optimization processing using the non-uniformity of the static magnetic field $B_0$ as a weight. According to the present MRI apparatus 100, the conductivity value can be calculated by the optimization processing that uses the structural similarity between the susceptibility map and conductivity map as a regulation parameter.

As can be seen from the above, according to the MRI apparatus 100 in the present embodiment, the regression parameter (inclination of the regression line) in phase distribution is calculated using a susceptibility image generated by the nonlinear processing to the phase image, the initial phase value $\varphi_0$ in the result of the regression analysis (regression line) is calculated using the calculated regression parameter (inclination) and phase distribution, and the conductivity map is generated using the calculated initial phase value $\varphi_0$. Thus, according to the present MRI apparatus 100, the error in the linear model of the phase value to the echo time can be reduced and a high-resolution conductivity map with reduced artifacts and noise can be generated.

FIRST APPLIED EXAMPLE

The difference with the present embodiment is that the susceptibility map and conductivity map is repeatedly generated until a stop condition for stopping an iterative processing for repeatedly generating the susceptibility map and the conductivity map is fulfilled.

The storage apparatus 129 stores the stop condition for stopping the iterative processing for repeatedly generating the susceptibility map and conductivity map. The stop condition is for example, the number of occurrences for repeating the generation of the susceptibility map and the conductivity map, the noise amount of the susceptibility map and/or conductivity map, an amount of change to the latest conductivity map from a conductivity map generated right before the generation of the latest conductivity map, and the amount of change to the latest susceptibility map from a susceptibility map generated before the latest susceptibility map. The number of occurrences can be input by an instruction of the operator through an interface circuit 125. In addition, for a noise amount of the conductivity map and/or susceptibility map, for example, the noise amount will be to a degree that is not visible by the operator in the display of the conductivity map and the susceptibility map. The amount of change is a value for example, in the vicinity of zero.

The processing circuitry 131 re-generates the susceptibility map by the susceptibility map generation function 1315, based on the conductivity value in the conductivity map generated by the conductivity map generation function 1317 and phase information (phase distribution). The processing circuitry 131 repeats the generation of a susceptibility map until the stop condition is fulfilled.

Specifically, the processing circuitry 131 calculates the initial phase value $\varphi_0$ using the conductivity value in the conductivity map and equation (8) by the susceptibility map generation function 1315. Equation (8) is equivalent to a Helmholtz equation; thus, the processing circuitry 131 analytically calculates the initial phase value $\varphi_0$ by a variable separation method, etc. The processing circuitry 131 is not limited to analytical calculation by the variable separation method as a calculation of the initial phase value $\varphi_0$; for example, the initial phase value $\varphi_0$ is calculated by a second optimization processing using the second evaluation function of at least one of equation (9), equation (10) and equation (11). When equation (10) is used as an evaluation function and the weighting coefficient $W_2$ is a noise amount of the susceptibility map, the noise amount of the latest susceptibility map of the repeated generated plurality of susceptibility maps is used as weighting coefficients $W_2$. When the equation (11) is used as an evaluation function, the processing circuitry 131 calculates similarity level $I(\sigma,\chi)$ using the latest susceptibility map and the latest conductivity map of the repeatedly generated plurality of conductivity maps.

The processing circuitry 131 executes further regression analysis for every pixel using an initial phase value $\varphi_0$ and phase distribution by the susceptibility map generation function 1315. For instance, the processing circuitry 131 executes fitting for every pixel by the regression analysis. The processing circuitry 131 updates the inclination of the regression line (regression parameter) in equation (1) by fitting. Next, the processing circuitry 131 calculates the susceptibility value using an updated inclination. The detailed explanation regarding the susceptibility value calculation will be omitted since it is similar to the matters explained in the embodiment. The processing circuitry 131 re-generates the susceptibility map using the calculated susceptibility value.

The processing circuitry 131 re-generates the conductivity map, based on the susceptibility value in the re-generated susceptibility map and phase information (phase distribution) by the conductivity map generation function 1317. The processing circuitry 131 repeatedly generates the conductivity map until the stop condition is fulfilled.

Specifically, the processing circuitry 131, by the conductivity map generation function 1317, converts the susceptibility value in the re-generated susceptibility map to an inclination of the regression line (regression parameter) by order transformation. The processing circuitry 131 updates the inclination in equation (1) to an order transformed inclination a'. In other words, the regression parameter a is updated to a new regression parameter a'. The processing circuitry 131 specifies and updates the initial phase value by a further regression analysis which uses the phase distribution and the updated inclination. The processing circuitry 131 calculates the conductivity value by using the updated initial phase value. The detailed explanation regarding the conductivity value calculation will be omitted since it is similar to the matters explained in the embodiment. The processing circuitry 131 re-generates the conductivity map using the calculated conductivity value.

Figure 6:
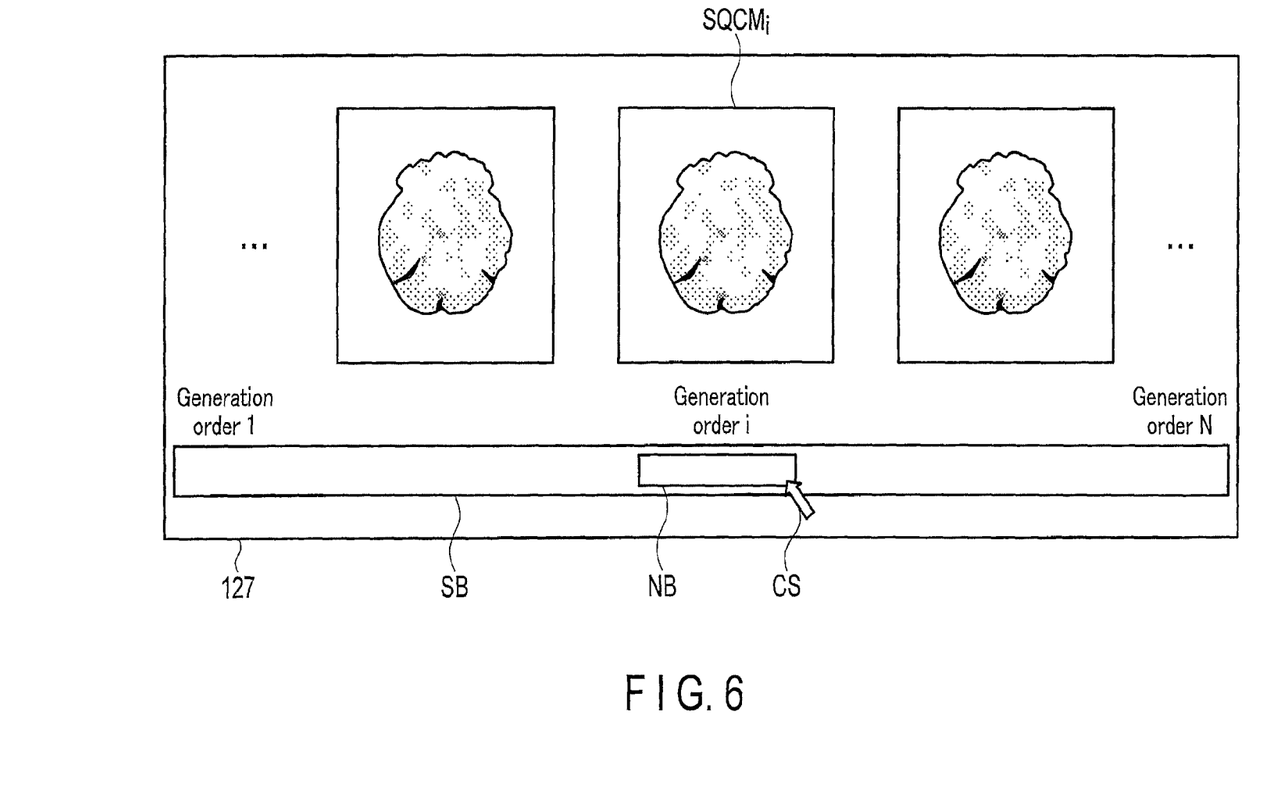
FIG. 6 is a diagram showing a displayed example of a plurality of conductivity superimposed images displayed arranged in generation order, and a display example of a knob of a scroll bar indicating a generation order according to a first applied example of the embodiment.

The display 127 displays the repeatedly generated plurality of susceptibility maps and/or plurality of conductivity maps with for example, a knob of a scroll bar indicating the generation order. FIG. 6 is a diagram showing a displayed example of a plurality of conductivity superimposed images displayed arranging in the generation order and displays a knob of a scroll bar indicating a generation order. The conductivity superimposed image $SQCM_i$ surrounded by a double line shown in FIG. 6 is a conductivity superimposed image generated in the i($1 \leq i \leq N$:i, N is a natural number)th iteration and shows a conductivity superimposed image selected by the operator through an interface circuitry 125. The conductivity superimposed image selected by the operator can be optionally emphasized displayed as a highlighted display, enlarged display, etc. instead of a double line frame. The knob NB in scroll bar SB indicates a position of number of occurrence i in a number of occurrences 1 to N shown in scroll bar SB. By the operation of the cursor CS through an interface circuitry 125, the conductivity superimposed image will be scrolled and displayed by moving the position of knob NB in the scroll bar SB. By this operation, the operator can select and display a desired image of the plurality of the susceptibility maps and plurality of conductivity maps.

(Operation)

The operation in the present applied example adds a processing of the processing circuitry 131 determining whether the stop condition is fulfilled after the processing of step Sa7 in flowchart of FIG. 3. Specifically, if the stop condition after the processing in step Sa7 is not fulfilled, the processings of step Sa3 to step Sa6 will be repeated. If the stop condition after the processing of step Sa7 is fulfilled, the repeatedly generated plurality of susceptibility maps and/or plurality of conductivity maps are displayed with the knob of the scroll bar indicating generation order. In this case, the selected susceptibility map or the conductivity map is stored in the storage apparatus 129 when the selection instruction of the operator is input through the interface circuitry 125 to the plurality of susceptibility maps and/or the plurality of conductivity maps.

According to the above-described configuration, the following advantageous effects can be obtained in addition to the advantageous effects described in the present embodiment.

According to the MRI apparatus 100 in the present applied example, the susceptibility map is re-generated based on the conductivity value in the generated conductivity map and the phase information, the conductivity map is re-generated based on the susceptibility value in the re-generated susceptibility map and the phase information, and the susceptibility map and/or the conductivity map are repeatedly generated until the stop condition for stopping the iterative processing for repeatedly generating the susceptibility map and the conductivity map is fulfilled. Specifically, according to the MRI apparatus 100 of the present applied example, the inclination of the regression line and initial phase value $\varphi_0$ in the phase distribution is updated for every repeated processing, the susceptibility map is generated using the updated inclination for every repeated processing and a conductivity map using an updated phase value is generated for every repeated processing until the stop condition is fulfilled. Thus, according to the MRI apparatus 100 of the present applied example, the error in the model of linearity of the phase value to the echo time can be further reduced and a high-resolution susceptibility map and conductivity map can be generated by further reducing the artifacts or the noise.

In addition, according to the MRI apparatus 100 of the present applied example, the repeatedly generated plurality of susceptibility maps and repeatedly generated plurality of conductivity maps can be displayed with a knob of the scroll bar indicating the generation order. By such structure, according to the present MRI apparatus 100, in the repeatedly generated plurality of susceptibility maps and plurality of conductivity maps, the operator can selectively display the desired susceptibility map and the conductivity map, for example, to improve the diagnostic efficiency to the subject P.

SECOND APPLIED EXAMPLE

The difference with the present embodiment is generating the conductivity map using the initial phase value $\varphi_0$ by fitting to the phase distribution, updating the initial phase value $\varphi_0$ using the generated conductivity map, and generating susceptibility map using an inclination by the fitting using the updated initial phase value $\varphi_0$. That is, in the present applied example, first the conductivity map based on phase distribution is generated, then the susceptibility map based on the generated conductivity map and phase distribution is generated. In the present applied example, the conductivity map used in the generation of the susceptibility map is not limited to the conductivity map generated by the conductivity map generation function 1317 and can, for example, be a conductivity map actually measured by the conductivity meter etc. in advance or can be a conductivity map generated in the past using the second optimization processing. The processing circuitry 131 reads a conductivity map used to generate a susceptibility map from a storage apparatus 129, or through a network.

The processing circuitry 131 executes, by the conductivity map generation function 1317, fitting for each pixel by a regression analysis to the phase distribution. The processing circuitry 131 determines an initial phase value $\varphi_0$ (regression parameter) in the regression line for every pixel. The processing circuitry 131 calculates the conductivity value for every pixel by the second optimization processing using the determined initial phase value $\varphi_0$. The detailed explanation regarding the conductivity value calculation will be omitted since it is similar to the matters explained in the embodiment. The processing circuitry 131 generates a conductivity map using the calculated conductivity value.

The processing circuitry 131 calculates the initial phase value $\varphi_0$ using the conductivity value in the conductivity map and equation (8) by the susceptibility map generation function 1315. When the conductivity map is generated by the conductivity map generation function 1317, the processing circuitry 131 updates the initial phase value $\varphi_0$ used in the generation of the conductivity map to the initial phase value $\varphi_0$ calculated by the susceptibility map generation function 1315.

The processing circuitry 131 executes fitting for each pixel by further regression analysis using the updated or calculated initial phase value $\varphi_0$ and phase distribution by the susceptibility map generation function 1315. The processing circuitry 131 calculates the inclination a of the regression line in equation (1) by fitting. The processing circuitry 131 calculates the susceptibility value using the calculated inclination a. The detailed explanation regarding susceptibility value calculation will be omitted since it is similar to the matters explained in the embodiment. The processing circuitry 131 generates the susceptibility map using the calculated susceptibility value.

(Operation)

Figure 7:
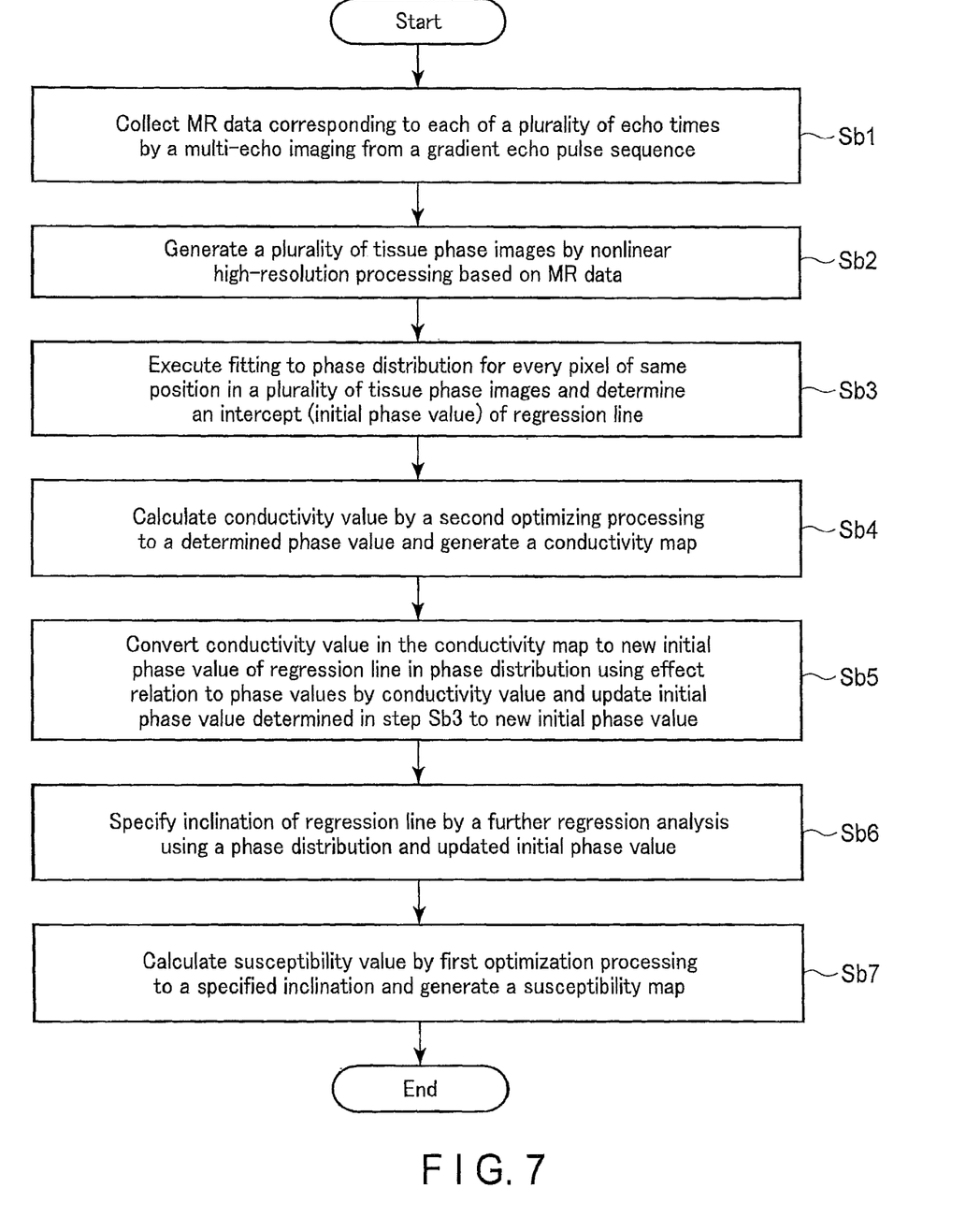
FIG. 7 is a flowchart showing an example of a processing of an operation according to the second applied example of the embodiment.

FIG. 7 is a flowchart showing an example of a process of the operation according to the present applied example. The explanation of the processing in step Sb1 and step Sb2 is omitted since it is similar to the processing of step Sa1 and step Sa2 in FIG. 3.

(Step Sb3)

The fitting is executed by regression analysis to the phase distribution for every pixel in the same position in the plurality of tissue phase images. By such fitting, the initial phase value $\varphi_0$ (regression parameter) in the regression line in equation (1) is determined for each pixel.

(Step Sb4)

The conductivity value by the second optimization processing to the determined phase value is calculated for every pixel. The conductivity map is generated using a plurality of conductivity values each corresponding to a plurality of pixels. When the noise amount of the conductivity mapping in the first optimization processing is used as weighting coefficient $W_1$, the variance of the conductivity map is calculated as the noise amount by the conductivity map generation function 1317.

(Step Sb5)

The conductivity value in the conductivity map converts to new initial phase value $\varphi_0$ of the regression line in the phase distribution by using the effect relation (equation (8)) to the phase values by conductivity. Next, the initial phase value determined in step Sb3 is updated to a converted new initial phase value $\varphi_0$. When the conductivity mapping is read through a storage apparatus 129 or a network, the conductivity value of the read conductivity map converts to the initial phase value $\varphi_0$ using equation (8). The processing of the hereinafter described step Sb6 will be executed using a converted initial phase value $\varphi_0$.

(Step Sb6)

The inclination of the regression line is specified by further regression analysis using the phase distribution and the updated initial phase value. Specifically, the intercept of the regression line is fixed to the initial phase value $\varphi_0$ calculated in step Sb5 to change the inclination of the regression line, and the inclination a is determined by applying the least squares method to the phase distribution.

(Step Sb7)

The susceptibility value is calculated for every pixel by the first optimization processing to the specified inclination. The susceptibility map is generated using a plurality of susceptibility values each corresponding to a plurality of pixels. In the present applied example, as shown in the first applied example, the susceptibility map and conductivity map can be repeatedly generated until the stop condition for stopping an iterative processing for repeatedly generating the susceptibility map and the conductivity map is fulfilled.

According to the above-described configuration, the following advantageous effects can be obtained.

In the MRI apparatus 100 according to the present applied example, the susceptibility value in the subject is calculated using the conductivity value in the conductivity map quantitatively indicating the plurality of conductivity in the subject, and generating a susceptibility map quantitatively indicating the plurality of susceptibility in the subject using the susceptibility value. In other words, the present MRI apparatus 100 converts the conductivity value to a intercept of the regression line in the distribution of the phase value to the echo time for every pixel using the effect relation to the phase information (spin phase value) by conductivity, specifies the inclination of the regression line by regression using the converted intercept and phase distribution, and calculates the susceptibility value using the specified inclination.

Thus, according to the present MRI apparatus 100, the error in the linear model of the phase values to the echo times can be reduced and a high-resolution susceptibility map with reduced artifacts and noise can be generated.

If the technical idea of the present MRI apparatus 100 is realized by a medical image processing apparatus 135 as a modification of the present embodiment and various applied examples, the medical processing apparatus 135 would include, for example, the constituent elements shown in the dashed line in the configuration diagram of FIG. 1. The medical image processing apparatus 135 performs various types of processing using MR data, susceptibility maps, or conductivity maps, etc. stored in the storage apparatus 129.

For example, the processing in step Sa1 of FIG. 3 and the processing in step Sb1 of FIG. 7 would be "read MR data from the storage apparatus 129." Furthermore, when the susceptibility map, nonlinearly processed against the MR data or actually measured by the susceptometer, etc. is stored in the storage apparatus 129, the processing of step Sa1 to step Sa4 in FIG. 3 will be omitted. When the conductivity map, nonlinearly processed against the MR data, or actually measured by the conductivity meter, etc. is stored in the storage apparatus 129, the processing of step Sb1 to step Sb4 in FIG. 7 will be omitted. Since advantageous effects achieved by the medical image processing apparatus 135 are the same as those achieved by the present embodiment, the description thereof is omitted.

In addition, the image generation function 1313, the susceptibility map generation function 1315, the conductivity map generation function 1317, etc. of the present embodiment and the applied examples can also be realized by installing a program (medical processing program) that executes these functions in a computer, such as a work station, and expanding these functions in a memory. In such a case, the medical processing program realizes, for example, calculating the conductivity value in the subject using the susceptibility value in the susceptibility map by quantitatively indicating the plurality of susceptibility in the subject, and generating a conductivity map quantitatively indicating the plurality of conductivity in the subject using the conductivity. The program that causes a computer to execute the above method can be stored and distributed on various types of portable storage medium such as a magnetic disc, an optical disc, or a semiconductor memory.

According to the MRI apparatus 100 and the medical processing apparatus 135 of the above mentioned embodiment, applied examples, and modification, etc., of a high-resolution and noise-reduced image which quantifies the electromagnetic properties of the tissue, can be realized.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A magnetic resonance imaging apparatus comprising:
processing circuitry configured to generate a conductivity map quantitatively indicating conductivity in a subject by using a susceptibility map quantitatively indicating susceptibility in the subject,
wherein the conductivity map is generated by order transforming the susceptibility map in accordance with Maxwell's equation,
wherein the susceptibility map is generated from magnetic resonance data with different echo times collected by a gradient echo pulse sequence, and
wherein the conductivity map is generated by converting a susceptibility value to an inclination of a regression line in a distribution of phase values to the echo times by using an effect relation to the phase values by the echo times and the susceptibility value.

2. The magnetic resonance imaging apparatus according to claim 1, wherein the processing circuitry calculates a conductivity value in the subject using a susceptibility value in the susceptibility map, and generates the conductivity map using the conductivity value.

3. The magnetic resonance imaging apparatus according to claim 1, wherein the processing circuitry generates the susceptibility map by a nonlinear processing of the phase values.

4. The magnetic resonance imaging apparatus according to claim 1, wherein the processing circuitry specifies a phase value in a point when an echo time is zero by regression using the distribution and the inclination, and calculates the conductivity using the specified phase value.

5. The magnetic resonance imaging apparatus according to claim 1, wherein the processing circuitry calculates a noise amount of the susceptibility map based on the susceptibility value in the susceptibility map, calculates a conductivity value by a weight optimization processing using the noise amount as a weight, and generates the conductivity map using the conductivity value.

6. The magnetic resonance imaging apparatus according to claim 1, wherein the processing circuitry generates the susceptibility map by removing non-uniformity of a static magnetic field in an imaging to the subject from the phase values, calculates a conductivity value by a weight optimization processing using the non-uniformity as a weight, and generates the conductivity map using the conductivity value.

7. The magnetic resonance imaging apparatus according to claim 1, wherein the processing circuitry calculates a conductivity value by an optimization processing using a structural similarity in the susceptibility map and the conductivity map as a regulation parameter, and generates the conductivity map using the conductivity value.

8. The magnetic resonance imaging apparatus according to claim 1, wherein the processing circuitry re-generates the susceptibility map based on conductivity value and the phase values in the generated conductivity map, and re-generates the conductivity map based on a susceptibility value and the phase values in the re-generated susceptibility map, and
the susceptibility map and/or the conductivity map are repeatedly generated until a stop condition to stop an iterative processing for repeatedly generating a susceptibility map and conductivity map is fulfilled.

9. The magnetic resonance imaging apparatus according to claim 8, further comprising a display that displays a repeatedly generated plurality of susceptibility maps and the repeatedly generated plurality of conductivity maps with a knob of a scroll bar indicating generation order.

10. A magnetic resonance imaging apparatus comprising processing circuitry calculating a susceptibility value in a subject using a conductivity value in conductivity map quantitatively indicating a plurality of conductivity in the subject, and generating a susceptibility map quantitatively indicating a plurality of susceptibility in the subject using the susceptibility, wherein the processing circuitry:
generates a plurality of phase images with different echo times based on a magnetic resonance data with different echo times, wherein each of the plurality of phase images includes a phase value in each of a plurality of pixels,
generates the conductivity map based on a phase distribution, wherein the phase distribution represents a spatial distribution of the phase value to the echo time concerning the plurality of pixels in the plurality of phase images, and
generates the susceptibility map based on the conductivity map and the phase distribution.

11. A medical imaging processing apparatus comprising:
a memory which stores a susceptibility map quantitatively indicating a plurality of susceptibility in a subject; and
processing circuitry configured to calculate a conductivity value in a subject using a susceptibility value in the susceptibility map and configured to generate a conductivity map quantitatively indicating a plurality of conductivity in the subject using the conductivity value,
wherein the conductivity map is generated by order transforming the susceptibility map in accordance with Maxwell's equation,
wherein the susceptibility map is generated from magnetic resonance data with different echo times collected by a gradient echo pulse sequence, and
wherein the conductivity map is generated by converting the susceptibility value to an inclination of a regression line in a distribution of phase values to the echo times by using an effect relation to the phase values by the echo times and the susceptibility value.

* * * * *